US008882890B2

(12) United States Patent
Rosser et al.

(10) Patent No.: US 8,882,890 B2
(45) Date of Patent: Nov. 11, 2014

(54) APPARATUSES AND METHODS FOR SEPARATING LIQUEFIABLE HYDROCARBONS FROM HYDROGEN-, HYDROCARBON-CONTAINING GAS STREAMS

(71) Applicant: UOP LLC, Des Plaines, IL (US)

(72) Inventors: Frank S. Rosser, LaGrange Park, IL (US); Larry D. Awe, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 169 days.

(21) Appl. No.: 13/728,568

(22) Filed: Dec. 27, 2012

(65) Prior Publication Data

US 2014/0187841 A1 Jul. 3, 2014

(51) Int. Cl.
*B01D 53/14* (2006.01)
*B01D 53/18* (2006.01)
*B01D 47/02* (2006.01)
*C07C 7/11* (2006.01)

(52) U.S. Cl.
CPC ............... *B01D 53/14* (2013.01); *B01D 47/02* (2013.01); *C07C 7/11* (2013.01); *B01D 2256/16* (2013.01); *B01D 2257/702* (2013.01); *B01D 53/18* (2013.01)
USPC ................... 95/237; 95/155; 96/243; 96/364; 62/617; 585/867; 422/260

(58) Field of Classification Search
CPC ........ B01D 47/02; B01D 53/14; B01D 53/18; B01D 2256/16; B01D 2257/702; C07C 7/11
USPC .............. 95/155, 237; 96/243, 266, 363, 364; 62/627; 585/867; 422/260
See application file for complete search history.

(56) References Cited

U.S. PATENT DOCUMENTS

| | | | | |
|---|---|---|---|---|
| 3,682,911 A | * | 8/1972 | Kaasenbrood et al. | 544/201 |
| 3,700,672 A | * | 10/1972 | Kokubo et al. | 544/201 |
| 4,138,560 A | * | 2/1979 | Hillenbrand et al. | 544/203 |
| 4,797,140 A | * | 1/1989 | Landeck et al. | 95/173 |
| 5,112,578 A | | 5/1992 | Murayama et al. | |
| 5,529,612 A | * | 6/1996 | Troost | 95/237 |
| 6,303,022 B1 | | 10/2001 | Rosser, Jr. | |
| 2012/0234167 A1 | * | 9/2012 | Castillo-Welter et al. | 96/243 |

FOREIGN PATENT DOCUMENTS

| | | |
|---|---|---|
| TW | 402517 B | 8/2000 |
| WO | 2011/088981 A1 | 7/2011 |
| WO | 2012/009965 A1 | 1/2012 |

* cited by examiner

*Primary Examiner* — Jason M Greene
(74) *Attorney, Agent, or Firm* — Mark R Willis

(57) ABSTRACT

Embodiments of apparatuses and methods for separating liquefiable hydrocarbons from $H_2$-, hydrocarbon-containing gas streams are provided. In one example, a method comprises positioning a $H_2$-, hydrocarbon-containing gas stream in an internal volume of a vessel below a heat exchange absorption section. A hydrocarbon-containing liquid stream is positioned in the internal volume above the heat exchange absorption section. The hydrocarbon-containing liquid stream is countercurrent contacted with at least a portion of the $H_2$-, hydrocarbon-containing gas stream along a tube portion of the heat exchange absorption section to separate $H_2$ and $C_3^+$ hydrocarbons. The hydrocarbon-containing liquid stream and the at least the portion of the $H_2$-, hydrocarbon-containing gas stream are cooled along the tube portion to facilitate separating $H_2$ and $C_3^+$ hydrocarbons.

20 Claims, 1 Drawing Sheet

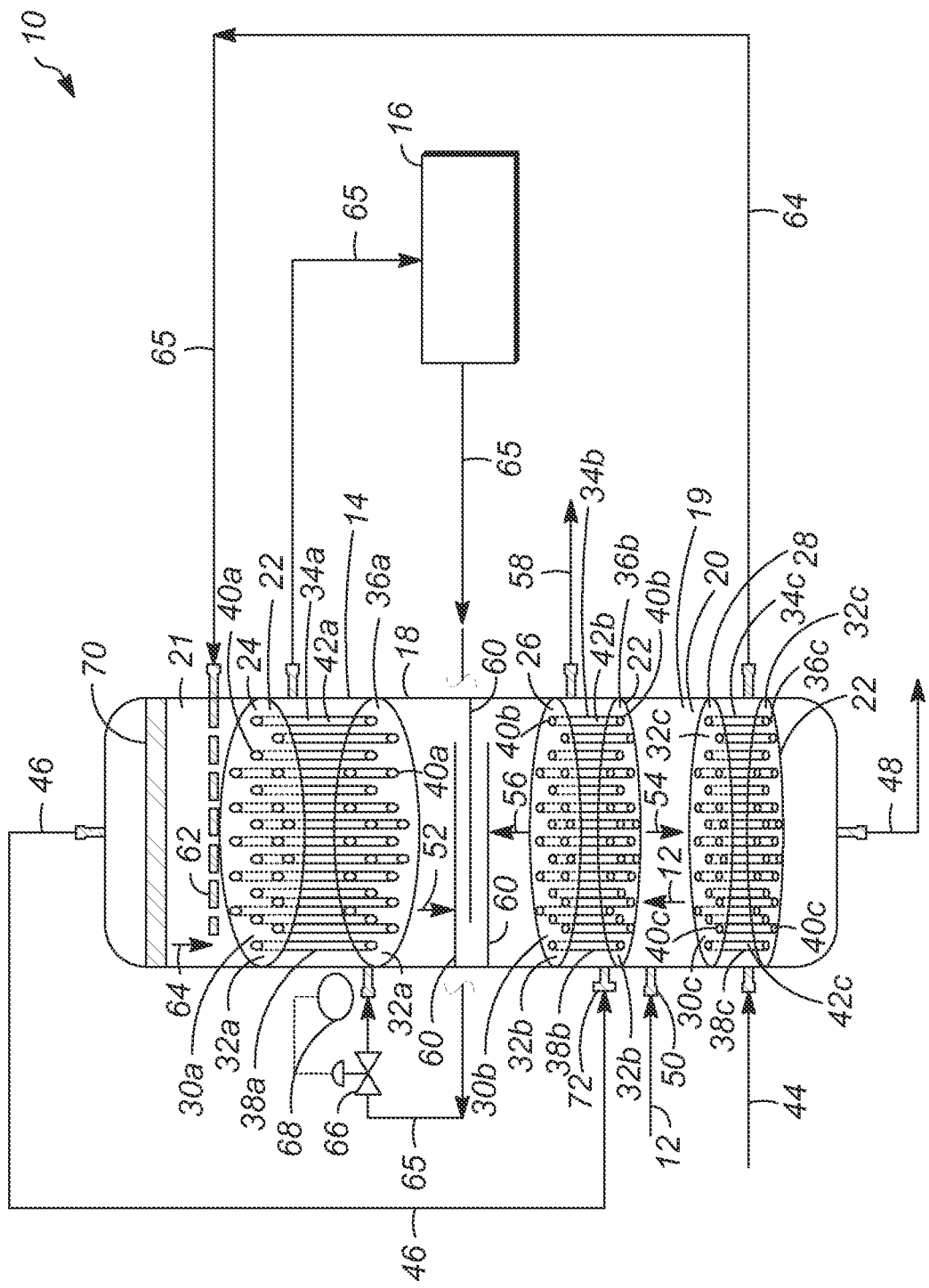

US 8,882,890 B2

APPARATUSES AND METHODS FOR SEPARATING LIQUEFIABLE HYDROCARBONS FROM HYDROGEN-, HYDROCARBON-CONTAINING GAS STREAMS

TECHNICAL FIELD

The technical field relates generally to apparatuses and methods for separating products from hydrocarbon conversion processes, and more particularly relates to apparatuses and methods for separating liquefiable hydrocarbons from hydrogen-, hydrocarbon-containing gas streams produced, for example, from catalytic reforming of hydrocarbons.

BACKGROUND

Various types of catalytic hydrocarbon conversion processes have found widespread utilization throughout the petroleum and petrochemical industries for affecting the conversion of hydrocarbons to different products. Often these conversion processes result in either the net production of hydrogen or the net consumption of hydrogen. Examples of net hydrogen-producing hydrocarbon conversion processes include catalytic reforming, catalytic dehydrogenation of alkylaromatics, and catalytic dehydrogenation of paraffins. Of these, catalytic reforming is one of the most widely employed.

Catalytic reforming of hydrocarbons is used by refiners for upgrading the octane rating of gasoline. In catalytic reforming, a hydrocarbon feedstock of, for example, $C_5$ hydrocarbons to about $C_{11}$ hydrocarbons, is contacted with a reforming catalyst to convert at least a portion of the heavier hydrocarbons to aromatic hydrocarbons to increase the octane content of gasoline. The catalytic reforming of the heavier hydrocarbons to produce a liquid reformate that contains $C_5^+$ hydrocarbons including aromatic hydrocarbons also produces significant quantities of valuable hydrogen and lighter hydrocarbons, such as liquefied petroleum gas (LPG) containing primarily $C_3$ and $C_4$ hydrocarbons, that form a hydrogen-, hydrocarbon-containing gas stream (e.g., net gas stream). Additionally, the hydrogen-, hydrocarbon-containing gas stream may also contain some unrecovered $C_5^+$ hydrocarbons. Some refiners currently separate hydrogen and liquefiable hydrocarbons, such as LPG and $C_5^+$ hydrocarbons, contained in a net gas stream using an elaborate and expensive sequence of vessels each performing a distinct unit operation for extracting and liquefying the $C_3^+$ hydrocarbons from the net gas stream. Refiners are looking for more efficient ways to maximize the recovery of hydrogen, LPG, and $C_5^+$ hydrocarbons from hydrogen-, hydrocarbon-containing gas streams.

Accordingly, it is desirable to provide apparatuses and methods for separating liquefiable hydrocarbons, such as $C_3^+$ hydrocarbons, from hydrogen-, hydrocarbon-containing gas streams produced, for example, from catalytic reforming of hydrocarbons. Furthermore, other desirable features and characteristics of the present invention will become apparent from the subsequent detailed description and the appended claims, taken in conjunction with the accompanying drawings and this background.

BRIEF SUMMARY

Methods and apparatuses for separating liquefiable hydrocarbons from $H_2$-, hydrocarbon-containing gas streams are provided herein. In accordance with an exemplary embodiment, an apparatus for separating liquefiable hydrocarbons from a $H_2$-, hydrocarbon-containing gas stream comprises a vessel. The vessel comprises a wall that extends vertically and that encloses an internal volume. A first heat exchange absorption section is disposed in the internal volume and has a first tube portion disposed in a first shell portion for thermal exchange with the first shell portion. The first tube portion is in fluid communication with the internal volume. The vessel is configured to position the $H_2$-, hydrocarbon-containing gas stream in the internal volume below the first heat exchange absorption section and a hydrocarbon-containing liquid stream in the internal volume above the first heat exchange absorption section for countercurrent contact of the hydrocarbon-containing liquid stream with at least a portion of the $H_2$-, hydrocarbon-containing gas stream along the first tube portion to separate $H_2$ and $C_3^+$ hydrocarbons. A refrigeration unit is in fluid communication with the first shell portion. The refrigeration unit is configured to advance a refrigerant through the first shell portion to cool the hydrocarbon-containing liquid stream and the at least the portion of the $H_2$-, hydrocarbon-containing gas stream along the first tube portion to facilitate separating $H_2$ and $C_3^+$ hydrocarbons and to form a chilled $H_2$-rich gas stream.

In accordance with another exemplary embodiment, an apparatus for separating liquefiable hydrocarbons from a $H_2$-, hydrocarbon-containing gas stream is provided. The apparatus comprises a vessel. The vessel comprises a wall extending vertically and enclosing an internal volume. An upper heat exchange absorption section is disposed in the internal volume and has an upper tube portion disposed in an upper shell portion for thermal exchange with the upper shell portion. A lower heat exchange absorption section is disposed in the internal volume below the upper heat exchange absorption section and has a lower tube portion disposed in a lower shell portion for thermal exchange with the lower shell portion. The upper and lower tube portions are in fluid communication with the internal volume. The vessel is configured to position the $H_2$-, hydrocarbon-containing gas stream in the internal volume below the lower heat exchange absorption section and a hydrocarbon-containing liquid stream in the internal volume above the upper heat exchange absorption section for countercurrent contact of the hydrocarbon-containing liquid stream with the $H_2$-, hydrocarbon-containing gas stream along the upper and lower tube portions to separate $H_2$ and $C_3^+$ hydrocarbons. The upper and lower shell portions are configured to receive a first chilled fluid and a second chilled fluid, respectively, to cool the $H_2$-, hydrocarbon-containing gas stream and the hydrocarbon-containing liquid stream to facilitate separating $H_2$ and $C_3^+$ hydrocarbons. A partially chilled, $H_2$-enriched hydrocarbon-containing gas stream disposed between the upper and lower heat exchange absorption sections is formed. Additionally, a $H_2$-rich gas stream disposed above the upper heat exchange absorption section and a $C_3^+$ hydrocarbon-rich liquid stream disposed below the lower heat exchange absorption section are formed.

In accordance with another exemplary embodiment, a method for separating liquefiable hydrocarbons from a $H_2$-, hydrocarbon-containing gas stream is provided. The method comprises the steps of positioning the $H_2$-, hydrocarbon-containing gas stream in an internal volume of a vessel below a heat exchange absorption section. A hydrocarbon-containing liquid stream is positioned in the internal volume above the heat exchange absorption section. The hydrocarbon-containing liquid stream is countercurrent contacted with at least a portion of the $H_2$-, hydrocarbon-containing gas stream along a tube portion of the heat exchange absorption section to separate $H_2$ and $C_3^+$ hydrocarbons. The hydrocarbon-containing liquid stream and the at least the portion of the $H_2$-, hydrocarbon-containing gas stream are cooled along the tube portion to facilitate separating $H_2$ and $C_3^+$ hydrocarbons and to form a chilled $H_2$-rich gas stream.

BRIEF DESCRIPTION OF THE DRAWINGS

The various embodiments will hereinafter be described in conjunction with the following drawing figures, wherein like numerals denote like elements, and wherein:

FIG. 1 schematically illustrates an apparatus and method for separating liquefiable hydrocarbons from a $H_2$-, hydrocarbon-containing gas stream in accordance with an exemplary embodiment.

DETAILED DESCRIPTION

The following Detailed Description is merely exemplary in nature and is not intended to limit the various embodiments or the application and uses thereof. Furthermore, there is no intention to be bound by any theory presented in the preceding background or the following detailed description.

Various embodiments contemplated herein relate to apparatuses and methods for separating liquefiable hydrocarbons from a hydrogen ($H_2$)-, hydrocarbon-containing gas stream. The exemplary embodiments taught herein provide an apparatus comprising a vessel that is configured for multiple unit operations. The vessel includes a heat exchange absorption section that is arranged in the internal volume of the vessel. In an exemplary embodiment, the heat exchange absorption section is formed of a tube-sheet arrangement comprising two vertically spaced apart sheets (e.g., flat plates) that are connected together by a plurality of tubes that extend between the sheets. The two sheets define a shell portion of the heat exchange absorption section and the tubes define a tube portion of the heat exchange absorption section. As such, the tube portion is disposed in the shell portion for thermal exchange with the shell portion. Additionally, the two sheets have a plurality of holes formed therethrough that are matched and aligned with the tubes such that the channels of the tubes are exposed to the internal volume of the vessel so that the tube portion is in fluid communication with the internal volume.

The vessel is configured to position a $H_2$-, hydrocarbon-containing gas stream in the internal volume below the heat exchange absorption section and a hydrocarbon-containing liquid stream in the internal volume above the heat exchange absorption section. In an exemplary embodiment, the hydrocarbon-containing liquid stream comprises $C_3^+$ hydrocarbons. As used herein, $C_x$ means hydrocarbon molecules that have "X" number of carbon atoms, $C_x^+$ means hydrocarbon molecules that have "X" and/or more than "X" number of carbon atoms, and $C_x^-$ means hydrocarbon molecules that have "X" and/or less than "X" number of carbon atoms. In one example, the hydrocarbon-containing liquid stream comprises primarily $C_5^+$ hydrocarbons and some $C_3$ and $C_4$ hydrocarbons and therefore, is relatively lean in $C_3$ and $C_4$ hydrocarbons so that the liquid stream effectively acts as a sponge liquid that readily absorbs $C_3$ and $C_4$ hydrocarbons.

Because the tube portion of the heat exchange absorption section is in open fluid communication with the internal volume of the vessel, the $H_2$-, hydrocarbon-containing gas stream can rise up into the tube portion, e.g., tube channels, while the hydrocarbon-containing liquid stream can flow downward into the tube portion, e.g., tube channels, for countercurrent contact between the liquid and gas streams along the tube portion. As such, $C_3^+$ hydrocarbons in the $H_2$-, hydrocarbon-containing gas stream are readily absorbed into the hydrocarbon-containing liquid stream, and $H_2$ and possibly some $H_2^-$ hydrocarbons in the hydrocarbon-containing liquid stream are readily absorbed into the $H_2$-, hydrocarbon-containing gas stream, thereby separating $H_2$ and $C_3^+$ hydrocarbons.

In an exemplary embodiment, a refrigeration unit is in fluid communication with the shell portion. The refrigeration unit advances a refrigerant through the shell portion to cool the hydrocarbon-containing liquid stream and the $H_2$-, hydrocarbon-containing gas stream along the tube portion during countercurrent contact of the streams to liquefy and remove $C_3^+$ hydrocarbons in the $H_2$-, hydrocarbon-containing gas stream, thereby facilitating separating $H_2$ and $C_3^+$ hydrocarbons for forming a $H_2$-rich gas stream and a $C_3^+$ hydrocarbon-rich liquid stream. Because multiple unit operations, e.g., absorption by countercurrent contact and further separation by chilling and liquefying hydrocarbons, are performed in a single vessel, recovery of $H_2$, LPG, and $C_5^+$ hydrocarbons from a hydrogen-, hydrocarbon-containing gas stream is efficiently and effectively achieved.

Referring to FIG. 1, an apparatus 10 for separating liquefiable hydrocarbons from a $H_2$-, hydrocarbon-containing gas stream 12 in accordance with an exemplary embodiment is provided. The apparatus 10 comprises a vessel 14 and a refrigeration unit 16 that is in fluid communication with the vessel 14.

The vessel 14 comprises a wall 18 that extends vertically and encloses an internal volume 19 that has a lower portion 20 extending to an upper portion 21. Disposed in the internal volume 19 are a plurality of heat exchange absorption sections 22 including a heat exchange absorption section 24, a heat exchange absorption section 26, and a heat exchange absorption section 28. While the vessel 14 is shown as having three heat exchange absorption sections 22, it is to be appreciated that the vessel 14 can have more than three heat exchange absorption sections or less than three heat exchange absorption sections but will have at least one heat exchange absorption section.

In an exemplary embodiment, the heat exchange absorption sections 22 are each formed of a tube-sheet arrangement 30a, 30b, or 30c that comprises two spaced apart sheets (e.g., horizontal flat plates) 32a, 32b, or 32c that are connected together by a plurality of tubes 34a, 34b, or 34c. The two sheets 32a, 32b, or 32c define a shell portion 36a, 36b, or 36c of the heat exchange absorption section 22 and the tubes 34a, 34b, or 34c define a tube portion 38a, 38b, or 38c of the heat exchange absorption section 22. As such, the tube portion 38a, 38b, or 38c is disposed in the shell portion 36a, 36b, or 36c for thermal exchange with the shell portion 36a, 36b, or 36c. Additionally, the two sheets 32a, 32b, or 32c have a plurality of holes 40a, 40b, or 40c formed therethrough that are matched and aligned with the tubes 34a, 34b, or 34c such that the channels 42a, 42b, or 42c of the tubes 34a, 34b, or 34c are exposed to the internal volume 19 of the vessel 14 so that the tube portion 38a, 38b, or 38c is in open fluid communication with the internal volume 19. In an exemplary embodiment, the tubes 34a, 34b, or 34c, independently or in combination, may include various inserts, grooved walls, or the like to enhance liquid-vapor contact as are known in the art.

As illustrated, the $H_2$-, hydrocarbon-containing gas stream 12 and a hydrocarbon-containing liquid stream 44 are introduced to the vessel 14. In an exemplary embodiment, the $H_2$-, hydrocarbon-containing gas stream 12 comprises $H_2$, $C_2^-$ hydrocarbons, $C_3$ and $C_4$ hydrocarbons, and some $C_5^+$ hydrocarbons. In one example, the $H_2$-, hydrocarbon-containing gas stream 12 comprises $H_2$ present in an amount of from about 80 to about 90 weight % (wt. %) and $C_2^-$ and $C_3^+$ hydrocarbons present in an amount of from about 10 to about 20 wt. % of the $H_2$-, hydrocarbon-containing gas stream 12.

In an exemplary embodiment, the hydrocarbon-containing liquid stream 44 comprises $C_3^+$ hydrocarbons. In one embodiment, the hydrocarbon-containing liquid stream 44 comprises predominantly $C_5$ and $C_6$ hydrocarbons and is relatively lean in $C_4^-$ hydrocarbons so that the hydrocarbon-containing liquid stream 44 effectively acts as a sponge liquid that readily absorbs $C_3$ and $C_4$ hydrocarbons. In one example, the $H_2$-, hydrocarbon-containing gas stream 12 and the hydrocarbon-containing liquid stream 44 are formed upstream from the vessel 14 by separating a reforming reactor effluent from a catalytic reforming process using a separator. The reforming reactor effluent is separated into the hydrocarbon-containing liquid stream 44 and a net gas stream that corresponds to the $H_2$-, hydrocarbon-containing gas stream 12. In an exemplary embodiment, the hydrocarbon-containing liquid stream 44 and the $H_2$-, hydrocarbon-containing gas stream 12 have a temperature of from about 25 to about 50° C.

As will be discussed in further detail below, the vessel 14 is configured to separate $H_2$ and $C_3^+$ hydrocarbons from the $H_2$-, hydrocarbon-containing gas stream 12 and the hydrocarbon-containing liquid stream 44 to form a chilled $H_2$-rich gas stream 46 and a partially heated $C_3^+$ hydrocarbon-rich liquid stream 48. In particular and as illustrated, the $H_2$-, hydrocarbon-containing gas stream 12 is advanced through an inlet 50 and is positioned in the internal volume 19 below the heat exchange absorption section 26. As such, the $H_2$-, hydrocarbon-containing gas stream 12 rises up into the tube portion 38b. As will be discussed in further detail below, above the heat exchange absorption section 26, a chilled partially-enriched $C_3^+$ hydrocarbon-containing liquid stream 52 from the heat exchange absorption section 24 falls downward into the tube portions 38b for countercurrent contact with the $H_2$-, hydrocarbon-containing gas stream 12. Along the tube portion 38b, the chilled partially-enriched $C_3^+$ hydrocarbon-containing liquid stream 52 and the $H_2$-, hydrocarbon-containing gas stream 12 are in intimate contact such that $H_2$ and $C_3^+$ hydrocarbons are separated. In an exemplary embodiment, $C_3^+$ hydrocarbons in the $H_2$-, hydrocarbon-containing gas stream 12 are readily absorbed into the chilled partially-enriched $C_3^+$ hydrocarbon-containing liquid stream 52, and $H_2$ and possibly some $H_2^-$ hydrocarbons in the hydrocarbon-containing liquid stream 52 are readily absorbed into the $H_2$-, hydrocarbon-containing gas stream 12.

As illustrated, the chilled $H_2$-rich gas stream 46 is removed from the upper portion 21 of the vessel 14 and is introduced to the heat exchange absorption section 26. In an exemplary embodiment, the chilled $H_2$-rich gas stream 46 has a temperature of from about −35 to about 0° C. The chilled $H_2$-rich gas stream 46 is passed through the shell portion 36b to cool the $H_2$-, hydrocarbon-containing gas stream 12 during countercurrent contact with the chilled partially-enriched $C_3^+$ hydrocarbon-containing liquid stream 52, causing $C_3^+$ hydrocarbons in the $H_2$-, hydrocarbon-containing gas stream 12 to liquefy into the chilled partially-enriched $C_3^+$ hydrocarbon-containing liquid stream 52 to form a partially chilled, further-enriched $C_3^+$ hydrocarbon-containing liquid stream 54 and a partially chilled, $H_2$-enriched hydrocarbon-containing gas stream 56. In an exemplary embodiment, the partially chilled, further-enriched $C_3^+$ hydrocarbon-containing liquid stream 54 has a temperature of from about −5 to about 20° C. and the partially chilled, $H_2$-enriched hydrocarbon-containing gas stream 56 has a temperature of from about −35 to about −10° C. In the shell portion 36b, the chilled $H_2$-rich gas stream 46 is heated to form a heated $H_2$-rich gas stream 58. In an exemplary embodiment, the heated $H_2$-rich gas stream 58 has a temperature of from about 25 to about 35° C. The heated $H_2$-rich gas stream 58 is removed from the vessel 14 and may be used, for example, elsewhere in the refinery for hydroprocessing, fuel, or the like.

The vessel 14 may also contain a plurality of contact trays 60 for separating $H_2$ and $C_3^+$ hydrocarbons. The contact trays 60 can be configured as sieve trays, fractionation trays, or the like as are well known in the art. As illustrated, the contact trays 60 are disposed between the heat exchange absorption sections 24a and 24b for further separating $H_2$ and $C_2^-$ hydrocarbons from the chilled partially-enriched $C_3^+$ hydrocarbon-containing liquid stream 52 and $C_3^+$ hydrocarbons from the partially chilled, $H_2$-enriched hydrocarbon-containing gas stream 56 as the streams 52 and 56 pass along the contact trays 60 in countercurrent flow.

The partially chilled, $H_2$-enriched hydrocarbon-containing gas stream 56 rises up into the tube portions 38a of the heat exchange absorption section 24. As will be discussed in further detail below, a distributor 62, which is disposed in the internal volume 19 above the heat exchange absorption section 24, distributes a partially cooled hydrocarbon-containing liquid stream 64 from the heat exchange absorption section 28 over the heat exchange absorption section 24. In an exemplary embodiment, the partially cooled hydrocarbon-containing liquid stream 64 has a temperature of from about 0 to about 20° C. The partially cooled hydrocarbon-containing liquid stream 64 falls downward into the tube portion 38a for countercurrent contact with the partially chilled, $H_2$-enriched hydrocarbon-containing gas stream 56.

Along the tube portion 38a, the partially cooled hydrocarbon-containing liquid stream 64 and the partially chilled, $H_2$-enriched hydrocarbon-containing gas stream 56 are in intimate contact such that $H_2$ and $C_3^+$ hydrocarbons are separated. In an exemplary embodiment, $C_3^+$ hydrocarbons in the partially chilled, $H_2$-enriched hydrocarbon-containing gas stream 56 are readily absorbed into the partially cooled hydrocarbon-containing liquid stream 64, and $H_2$ and possibly some $H_2^-$ hydrocarbons in the partially cooled hydrocarbon-containing liquid stream 64 are readily absorbed into the partially chilled, $H_2$-enriched hydrocarbon-containing gas stream 56.

In an exemplary embodiment, the refrigeration unit 16 compresses and condenses a refrigerant 65, such as propane or the like, that is passed along to a flash valve 66. The flash valve 66 controllably flashes or introduces the refrigerant 65 into the shell portion 36a as a chilled two-phase fluid in response to a level control 68 to cool the partially cooled hydrocarbon-containing liquid stream 64 and the partially chilled, $H_2$-enriched hydrocarbon-containing gas stream 56 along the tube portion 38a during countercurrent contact. This causes $C_3^+$ hydrocarbons in the partially chilled, $H_2$-enriched hydrocarbon-containing gas stream 56 to liquefy into the partially cooled hydrocarbon-containing liquid stream 64 to form the chilled $H_2$-rich gas stream 46 and the chilled partially-enriched $C_3^+$ hydrocarbon-containing liquid stream 52.

As illustrated, the vessel 14 may comprise a mesh pad 70 disposed in the internal volume 19 above the heat exchange absorption section 24 and the distributor 62. The mesh pad 70 removes residual liquid from the chilled $H_2$-rich gas stream 46. The chilled $H_2$-rich gas stream 46 is then removed from the upper portion 21 of the vessel 14 and is passed along to the inlet 72 for introduction to the heat exchange absorption section 26 as discussed above.

In an exemplary embodiment, the partially chilled, further-enriched $C_3^+$ hydrocarbon-containing liquid stream 50 descends downward from the heat exchange absorption section 26 into the tube portion 38c of the heat exchange absorption section 28. The hydrocarbon-containing liquid stream 44 is passed through the shell portion 36c and is cooled by the partially chilled, further-enriched $C_3^+$ hydrocarbon-containing liquid stream 50 to form the partially cooled hydrocarbon-containing liquid stream 64. As discussed above, the partially cooled hydrocarbon-containing liquid stream 64 is removed from the heat exchange absorption section 28 and is passed along to the distributor 62. Due to the thermal exchange in the heat exchange absorption section 28, the partially chilled, further-enriched $C_3^+$ hydrocarbon-containing liquid stream 50 is heated along the tube portion 38c to release $H_2$ and/or $C_2^-$ hydrocarbons as a rising gas phase and to form a partially heated $C_3^+$ hydrocarbon-rich liquid stream 48. In an exemplary embodiment, the partially heated $C_3^+$ hydrocarbon-rich liquid stream 48 has a temperature of from about 25 to about 35° C. The partially heated $C_3^+$ hydrocarbon-rich liquid stream 48 is removed from the vessel and may be passed along, for example, to a stabilizer to separate the stream into a LPG stream that is rich in $C_3$ and $C_4$ hydrocarbons and a raffinate stream that is rich in $C_5^+$ hydrocarbons.

Accordingly, apparatuses and methods for separating liquefiable hydrocarbons from a $H_2$-, hydrocarbon-containing gas stream have been described. The exemplary embodiments taught herein provide an apparatus comprising a vessel that includes a heat exchange absorption section arranged in the internal volume of the vessel. The heat exchange absorption section has a tube portion disposed in a shell portion for thermal exchange with the shell portion. The tube portion is in fluid communication with the internal volume. The vessel is configured to position the $H_2$-, hydrocarbon-containing gas stream in the internal volume below the heat exchange absorption section and a hydrocarbon-containing liquid stream in the internal volume above the heat exchange absorption section for countercurrent contact of the hydrocarbon-containing liquid stream with at least a portion of the $H_2$-, hydrocarbon-containing gas stream along the tube portion to separate $H_2$ and $C_3^+$ hydrocarbons. In an exemplary embodiment, a refrigeration unit is in fluid communication with the shell portion. The refrigeration unit is configured to advance a refrigerant through the shell portion to cool the hydrocarbon-containing liquid stream and the at least the portion of the $H_2$-, hydrocarbon-containing gas stream along the tube portion to facilitate separating $H_2$ and $C_3^+$ hydrocarbons and to form a chilled $H_2$-rich gas stream.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:
1. An apparatus for separating liquefiable hydrocarbons from a $H_2$-, hydrocarbon-containing gas stream, the apparatus comprising:
   a vessel comprising:
      a wall extending vertically and enclosing an internal volume; and
      a first heat exchange absorption section disposed in the internal volume and having a first tube portion disposed in a first shell portion for thermal exchange with the first shell portion, wherein the first tube portion is in fluid communication with the internal volume, and wherein the vessel is configured to position the $H_2$-, hydrocarbon-containing gas stream in the internal volume below the first heat exchange absorption section and a hydrocarbon-containing liquid stream in the internal volume above the first heat exchange absorption section for countercurrent contact of the hydrocarbon-containing liquid stream with at least a portion of the $H_2$-, hydrocarbon-containing gas stream along the first tube portion to separate $H_2$ and $C_3^+$ hydrocarbons; and
   a refrigeration unit in fluid communication with the first shell portion and configured to advance a refrigerant through the first shell portion to cool the hydrocarbon-containing liquid stream and the at least the portion of the $H_2$-, hydrocarbon-containing gas stream along the first tube portion to facilitate separating $H_2$ and $C_3^+$ hydrocarbons and to form a chilled $H_2$-rich gas stream.

2. The apparatus of claim 1, wherein the chilled $H_2$-rich gas stream has a temperature of from about −35 to about 0° C.

3. The apparatus of claim 1, wherein the refrigeration unit is configured to advance the refrigerant into the first shell portion to cool the hydrocarbon-containing liquid stream to form a chilled partially-enriched $C_3^+$ hydrocarbon-containing liquid stream.

4. The apparatus of claim 3, wherein the chilled partially-enriched $C_3^+$ hydrocarbon-containing liquid stream has a temperature of from about −35 to about 0° C.

5. The apparatus of claim 1, wherein the vessel comprises:
   a second heat exchange absorption section disposed in the internal volume below the first heat exchange absorption section and having a second tube portion disposed in a second shell portion for thermal exchange with the second shell portion, wherein the second tube portion is in fluid communication with the internal volume, wherein the vessel is configured to position the $H_2$-, hydrocarbon-containing gas stream in the internal volume below the second heat exchange absorption section for countercurrent contact of at least a portion of the hydrocarbon-containing liquid stream with the $H_2$-, hydrocarbon-containing gas stream along the second tube portion to separate $H_2$ and $C_3^+$ hydrocarbons, and wherein the apparatus is configured to advance the chilled $H_2$-rich gas stream through the second shell portion to cool the $H_2$-, hydrocarbon-containing gas stream along the second tube portion to facilitate separating $H_2$ and $C_3^+$ hydrocarbons.

6. The apparatus of claim 5, wherein the vessel comprises:
   a plurality of contact trays disposed in the internal volume between the first and second heat exchange absorption sections for separating $H_2$ and $C_3^+$ hydrocarbons from the at least the portion of the hydrocarbon-containing liquid stream and the at least the portion of the $H_2$-, hydrocarbon-containing gas stream.

7. The apparatus of claim 5, wherein the refrigeration unit is configured to advance the refrigerant into the first shell portion to cool the hydrocarbon-containing liquid stream to form a chilled partially-enriched $C_3^+$ hydrocarbon-containing liquid stream, and wherein the second heat exchange absorption section is configured to receive the chilled partially-enriched $C_3^+$ hydrocarbon-containing liquid stream along the second tube portion in countercurrent contact with the H$_2$, hydrocarbon-containing gas stream to form a partially chilled, further-enriched C$_3$$^+$ hydrocarbon-containing liquid stream.

8. The apparatus of claim 7, wherein the partially chilled, further-enriched C$_{3+}$ hydrocarbon-containing liquid stream has a temperature of from about −5 to about 20° C.

9. The apparatus of claim 7, wherein the vessel comprises:
a third heat exchange absorption section disposed in the internal volume below the second heat exchange absorption section and having a third tube portion disposed in a third shell portion for thermal exchange with the third shell portion, wherein the third tube portion is in fluid communication with the internal volume, wherein the third heat exchange absorption section is configured such that the third tube portion receives the partially chilled, further-enriched C$_3$$^+$ hydrocarbon-containing liquid stream and the third shell portion receives the hydrocarbon-containing liquid stream to cool the hydrocarbon-containing liquid stream and form a partially cooled hydrocarbon-containing liquid stream, and wherein the vessel is configured to advance the partially cooled hydrocarbon-containing liquid stream to above the first heat exchange absorption section for countercurrent contact with the at least the portion of the H$_2$-, hydrocarbon-containing gas stream.

10. The apparatus of claim 9, wherein the partially cooled hydrocarbon-containing liquid stream has a temperature of from about 0 to about 20° C.

11. The apparatus of claim 9, wherein the third heat exchange absorption section is configured such that the partially chilled, further-enriched C$_3$$^+$ hydrocarbon-containing liquid stream is heated along the third tube portion to release H$_2$ and/or C$_2$ hydrocarbons and form a partially heated C$_3$$^+$ hydrocarbon-rich liquid stream.

12. The apparatus of claim 11, wherein the partially heated C$_3$$^+$ hydrocarbon-rich liquid stream has a temperature of from about 25 to about 35° C.

13. The apparatus of claim 9, wherein the vessel is configured to position the H$_2$-, hydrocarbon-containing gas stream in the internal volume above the third heat exchange absorption section.

14. The apparatus of claim 9, wherein the third heat exchange absorption section is configured to receive the hydrocarbon-containing liquid stream as a sponge liquid having a temperature of from about 25 to about 50° C.

15. The apparatus of claim 1, wherein the vessel comprises:
a mesh pad disposed in the internal volume above the first heat exchange absorption section for removing liquid from the chilled H$_2$-rich gas stream.

16. The apparatus of claim 1, wherein the vessel comprises:
a distributor disposed in the internal volume above the first heat exchange absorption section and configured for distributing the hydrocarbon-containing liquid stream above the first heat exchange absorption section.

17. An apparatus for separating liquefiable hydrocarbons from a H$_2$-, hydrocarbon-containing gas stream, the apparatus comprising:
a vessel comprising:
a wall extending vertically and enclosing an internal volume;
an upper heat exchange absorption section disposed in the internal volume and having an upper tube portion disposed in an upper shell portion for thermal exchange with the upper shell portion; and
a lower heat exchange absorption section disposed in the internal volume below the upper heat exchange absorption section and having a lower tube portion disposed in a lower shell portion for thermal exchange with the lower shell portion, wherein the upper and lower tube portions are in fluid communication with the internal volume, wherein the vessel is configured to position the H$_2$-, hydrocarbon-containing gas stream in the internal volume below the lower heat exchange absorption section and a hydrocarbon-containing liquid stream in the internal volume above the upper heat exchange absorption section for countercurrent contact of the hydrocarbon-containing liquid stream with the H$_2$-, hydrocarbon-containing gas stream along the upper and lower tube portions to separate H$_2$ and C$_3$$^+$ hydrocarbons, wherein the upper and lower shell portions are configured to receive a first chilled fluid and a second chilled fluid, respectively, to cool the H$_2$-, hydrocarbon-containing gas stream and the hydrocarbon-containing liquid stream to facilitate separating H$_2$ and C$_3$$^+$ hydrocarbons and to form a partially chilled, H$_2$-enriched hydrocarbon-containing gas stream disposed between the upper and lower heat exchange absorption sections and for forming a H$_2$-rich gas stream disposed above the upper heat exchange absorption section and a C$_3$$^+$ hydrocarbon-rich liquid stream disposed below the lower heat exchange absorption section.

18. The apparatus of claim 17, wherein the vessel is configured to receive the H$_2$-, hydrocarbon-containing gas stream having a temperature of from about 25 to about 50° C.

19. The apparatus of claim 17, wherein the partially chilled, H$_2$-enriched hydrocarbon-containing gas stream has a temperature of from about −35 to about −10° C.

20. A method for separating liquefiable hydrocarbons from a H$_2$-, hydrocarbon-containing gas stream, the method comprising the steps of:
positioning the H$_2$-, hydrocarbon-containing gas stream in an internal volume of a vessel below a heat exchange absorption section;
positioning a hydrocarbon-containing liquid stream in the internal volume above the heat exchange absorption section;
countercurrent contacting the hydrocarbon-containing liquid stream with at least a portion of the H$_2$-, hydrocarbon-containing gas stream along a tube portion of the heat exchange absorption section to separate H$_2$ and C$_3$$^+$ hydrocarbons; and
cooling the hydrocarbon-containing liquid stream and the at least the portion of the H$_2$-, hydrocarbon-containing gas stream along the tube portion to facilitate separating H$_2$ and C$_3$$^+$ hydrocarbons and to form a chilled H$_2$-rich gas stream.

* * * * *